US005702943A

United States Patent [19]
Ehret

[11] Patent Number: 5,702,943
[45] Date of Patent: *Dec. 30, 1997

[54] PROCESS FOR PREPARING A BIOMASS ON A CEREAL MEDIUM, USE OF THE PRODUCTS SO PREPARED AND PANIFICATION FERMENT

[75] Inventor: Aloyse Ehret, Blotzheim, France

[73] Assignee: Agrano AG, Allschwil, Switzerland

[*] Notice: The term of this patent shall not extend beyond the expiration date of Pat. No. 5,700,684.

[21] Appl. No.: 440,767

[22] Filed: May 15, 1995

[30] Foreign Application Priority Data

May 27, 1994 [EP] European Pat. Off. ............ 94810307

[51] Int. Cl.$^6$ .............. A23L 1/28; A23L 1/221; C12N 1/20
[52] U.S. Cl. .......... 435/253.6; 426/18; 426/61; 426/549; 426/650; 435/174; 435/178; 435/252.9; 435/260
[58] Field of Search .................. 435/174, 178, 435/252.9, 253.6, 260, 855; 426/18, 61, 549, 650

[56] References Cited

U.S. PATENT DOCUMENTS

| | | | |
|---|---|---|---|
| 4,745,062 | 5/1988 | Guerineau et al. | 435/209 |
| 4,844,935 | 7/1989 | Fere et al. | 426/549 |
| 4,925,693 | 5/1990 | Lauly | 426/549 |
| 5,200,215 | 4/1993 | Slade et al. | 426/18 |
| 5,211,971 | 5/1993 | Van Dijk et al. | 426/18 |
| 5,231,017 | 7/1993 | Lantero et al. | 435/161 |
| 5,283,069 | 2/1994 | Van Dijk et al. | 426/18 |
| 5,362,502 | 11/1994 | Slade et al. | 426/20 |
| 5,458,415 | 10/1995 | Poilaane | 366/138 |

*Primary Examiner*—David M. Naff
*Assistant Examiner*—Deborah K. Ware
*Attorney, Agent, or Firm*—Tarolli, Sundheim, Cove Tummino & Szab

[57] ABSTRACT

A biomass which can be used directly as panification ferment without previous separation of the culture medium and the biomass and without addition of industrial yeast is prepared by cultivating at least one strain of yeast in a culture medium specified in the description. Preferably, the said ferment comprises as yeast the strain *Saccharomyces cerevisiae steineri* DSM 9211.

10 Claims, No Drawings

PROCESS FOR PREPARING A BIOMASS ON A CEREAL MEDIUM, USE OF THE PRODUCTS SO PREPARED AND PANIFICATION FERMENT

FIELD OF THE INVENTION

This invention refers to a process for preparing a biomass on a cereal medium, the obtained product being directly usable as a panification ferment without previous separation of the culture medium and the biomass; to the use of the biomass so prepared as panification ferment; to the use of the supernatent resulting from said process; as well as to a panification ferment.

BACKGROUND OF THE INVENTION

Actually, the yeast used in the panification is obtained industrially from cultures made from molasses of beetroots or sugar cane mediums, supplemented by vitamins and by chemical compounds, such as phosphoric acid and ammonia. This yeast, separated by centrifugation and par filtration, allows a quick panification, but it does not confer to the finished product of the process the organoleptic properties which are found in a home baked bread from a sponge.

SUMMARY OF THE INVENTION

A first object of the present invention is to eliminate said disadvantages of the prior art.

Another object of the present invention is to create a biomass on a cereal medium, the obtained product being directly usable as an industrial panification ferment without preliminary separation of the culture medium and the biomass and without addition of so-called industrial yeast.

The foregoing and other objects, advantages and features of the present invention can be attained by a process wherein at least one strain of yeast is cultivated on a culture medium obtained by double hydrolysis of a diluted aqueous mixture containing at least whole-flour and/or wheat germs, namely by total hydrolysis of the starch into fermentable sugars by the action of at least one alpha-amylase and at least one amyloglucosidase, and by gentle hydrolysis of at least part of the gluten by proteolytic enzymes of food quality, said culture medium being free of any chemical additives.

Effecting said culture in the culture medium described above garantees that the obtained panification products present particularly approved organoleptic qualities.

Preferably, the culture is of the discontinued alimented type, called "fed-batch". This technique consists of adding periodically and continuously adding a batch of the milieu together with the necessary ingredients. This type of fermentation allows to control the metabolism of the culture between the aerobic and the anaerobic pathway, thus controlling the metabolic flux between growth (biomass) and the products derived from its metabolism (especially ethanol).

Preferably, the culture is made without pH regulation, thus avoiding the addition of any chemical additives.

Preferably, the ethanol content of the culture is controlled by regulation of the alimentation speed of the culture medium.

The partial pressure of the oxygen dissolved in the culture can be controlled by regulating the air supply and/or by regulating the agitation speed, in accordance with a previously defined slope, while maintaining the culture in a metabolism limited in oxygen.

Preferably, the yeast used is a strain of *Saccharomyces cerevisiae*, and especially a strain isolated from a natural sponge, particularly the strain *Saccharomyces cerevisiae steineri* DSM 9211. This strain was isolated from a home made sponge of an excellent organoleptic quality. The characteristics of the type *Saccharomyces cerevisiae* are compiled in Table 1.

Table 1

Characteristics of *Saccharomyces cerevisiae*

Culture in a liquid medium (dosage medium diluted to one half):

Observation under the microscope: The yeast cells are oval (2 to 4×5 to 7 micrometers) and divide by multipolar budding.

Culture in a solid medium (dosage medium diluted to one half and added by 15 grams/liter of agar):

Observation of the colonies: The yeast colonies are round, smooth, mat, slightly ventricose, and cream-colored.

Metabolism of the sugars:

|  | Assimilation | Fermentation |
|---|---|---|
| Glucose | + | + |
| L-Arabinose | − | − |
| D-Xylose | − | − |
| Galactose | + | + |
| Cellobiose | − | − |
| Lactose | − | − |
| Maltose | + | + |
| Saccharose | + | + |
| Trehalose | − | − |
| Melezitose | − | − |
| Raffinose | + | − |

Preferably, the process of the present invention is executed in a bioreactor as follows:

introducing the culture medium into the bioreactor;

inoculating this culture medium with the yeast; and continuously alimenting the bioreactor with the culture medium;

while maintaining a temperature of about 30° C., an aeration controlled by the partial pressure of oxygen, and an ethanol concentration between 0.5 and 10 grams/liter of culture.

The product obtained can immediately be used when it comes out of the bioreactor as panification ferment for direct industrial use without further operation, such as previous separation of the culture medium and the biomass. However, it is generally preferable to concentrate the product by centrifugation or by filtration, since this reduces the water content in the product, which then can be stored below 3° C. for 21 days without noticeable loss of its rising capacity.

Also, in this case, the supernatant resulting from this concentration can be used for the preparation of a substrate for cultures of lactic acid bacteria, or for the preparation of a beverage.

EXAMPLE 5 liters of a culture medium, called "base medium", of the composition described hereafter, is introduced into a bioreactor of 15 liters, having an useful capacity of 10 liters:

5 liters of water;

a source of nitrogen, e.g. 250 grams of wheat germs;

a source of vitamins, amino acids and of mineral salts, e.g. 35 grams of yeast autolysate; and 15 grams of sea salt.

A strain of yeast identified as *Saccharomyces cerevisiae steineri*, deposited with the German Collection of Microorganisms (DMS) under No. 9211, is added to this medium. This strain was cultivated on a medium, called "dosage medium", having the following composition:

4 liters of water;
a carbon source, e.g. 800 grams of ground wheat kernels;
a nitrogen source, e.g. 500 grams of wheat germs;
a source of vitamins, of amino acids and of mineral salts, e.g. 70 grams of yeast autolysate; and
15 grams of sea salt.

The strain is stored at −80° C. in the cereal medium (dosage medium diluted to one half with water). The strain is reisolated on the solid cereal medium, and is entertained on the same medium by successive reinoculation every 15 days.

An isolated colony is inoculated in the liquid cereal medium. A second culture is made with 20 milliliters of the first one in a Erlenmeyer of 500 milliliters containing 200 milliliters of cereal medium. The cellular density obtained after 16 hours of culture with agitation is $3 \cdot 10^8$ CFU (CFU=Colonies for unit). per milliliter. A third culture is made from the second one with 600 milliliters of the previous culture. The cellular density obtained after 8 hours à 30° C. is $2.5 \cdot 10^8$ CFU per milliliter. The glucose is completely metabolized, and the measured ethanol content is near 25 grams/liter.

600 milliliters of this culture of yeast in an exponential phase are added to 5 liters of the base medium. The mixture is continuously alimented with dosage medium. The temperature is maintained at 30° C. The pH is continuously measured and not controlled, and the $pO_2$ is kept above 30%.

The alimentation speed is determined by two parameters which are essential for the good course of the process:

(a) The parameter ethanol concentration of the culture medium

Yeast is a microorganism capable of multiplying in aerobiose and/or in anaerobiose. The aerobic metabolism is favorable to the growth of the biomass, whereas the anaerobic metabolism leads to the production of ethanol and of secondary derivatives searched for their organoleptic qualities. The process according to the present invention permits to control the metabolic flow between these two extreme ways, permitting a good growth and therefor obtain a final biomass which is capable of being used in the direct panification under "industrial" time conditions.

The production of ethanol indicates a metabolic flow into the anaerobic pathway.

In the described process, the ethanol concentration is systematically examined and maintained between 0.5 and 10 grams/liter. If the ethanol concentration drops below the limit of 0.5 grams/liter, the alimentation speed of the dosage medium is raised. On the other hand, the alimentation speed of the dosage medium is reduced if the ethanol concentration exceeds the limit of 10 grams/liter.

(b) The aeration of the culture medium

This parameter is continuously determined by continuously measuring dissolved oxygen, and is controlled in two ways, i.e. by controlling the entry of air into the bioreactor and/or by diminishing the rotation speed of two agitator blades of the Rushton type (Size of the blades: one half of the diameter of the bioreactor), allowing the control of the transfer of $O_2$.

In the described process, the partial pressure of $O_2$ is kept above 10%. The agitation speed varies from 500 à 1200 rpm, and the exit of sterile air is from 0 to 30 liters/minute.

Under the described conditions, the culture is fed during 16 hours. The total alimentation during this period is 4 liters. The cellular density of the yeast reaches $2 \cdot 10^9$ cells per milliliter (density at start: $2.5 \cdot 10^7$ cells per milliliter).

The obtained culture is rapidly cooled to 3° C. and can then be kept without noticeable loss of its qualities for 21 days.

Variant

A postfermentation on flour in the ratio of 50 to 300 grams/liter of ferment for 6 hours at 20° C., followed by a cooling to 3° C. allows a storage during 30 days, and the obtaining of a panification product having the organoleptic qualities of the "sponge" type.

Panification

The liquid ferments (obtained directly from the bioreactor or after postfermentation) are used directly in a concentration of 20% (weight of flour/volume of ferment) for making a traditional dough from flour, water and salt.

Variant

The ferments are centrifuged. The reduction of their water content raises their stability and allows to considerably diminish the concentration in the panification process. Thus, a centrifugation at 8,500 g (gravity) makes it possible to obtain a ferment containing 75% of water which can be used in a concentration of 6 to 8% in the panification mixture.

The density of the obtained breads is identical with that of bread obtained by using the traditional pressed yeast (cultivated on sugary molasses) and used in a concentration of 2 to 3% on the weight of flour.

The analysis of the above Example is compiled in Table 2.

| \multicolumn{2}{c}{Taxonomy of *Saccharomyces cerevisiae steineri* strain DSM 9211 (Morphological and physiological characteristics)} |  |
|---|---|
| Yeast Morphology Agar | Form of colony: Smooth, glossy, whole-edge, white |
| Malt Bouillon | Cell form: Oval-shaped, multipolarly sprouting |
| Cornmeal Agar | No pseudomycelium |
| Malt Agar, V8 Agar | Asci formation: 2 to 4 ascospores per ascus; ascospores being round and smooth, ascus formation directly out from the vegetative cell |

| Assimilation and Fermentation (Percentage of positively reacting isolates) | | |
|---|---|---|
| Substrates | Fermentation | Assimilation |
| Glucose | 100 | 100 |
| Galactose | 100 | 100 |
| Saccharose | 100 | 100 |
| Maltose | 100 | 100 |
| Lactose | 0 | 0 |
| Raffinose | 0 | 100 |
| Starch | 0 | 0 |
| Melibiose | 0 | 0 |
| Nitrate |  | 0 |
| Trehalose | 0 | 0 |
| Cellobiose | 0 | 0 |
| L-Arabinose | 0 | 0 |
| D-Xylose | 0 | 0 |

TABLE 2

| Hours | Temperature °C. | Agitation rpm | Air flow l/min | $pO_2$ | pH | Ethanol g/l | Dosage % | Numeration $\times 10^8$ CFU/ml |
|---|---|---|---|---|---|---|---|---|
| 0  | 30 | 500  | 15 | 86.3 | 6.00 | 2.12 | 0   | 0.25  |
| 2  | 30 | 500  | 15 | 80.4 | 5.70 | 2.71 | 2   | 0.48  |
| 4  | 30 | 500  | 15 | 70.1 | 5.50 | 3.58 | 4   | 0.99  |
| 6  | 30 | 500  | 15 | 59.1 | 5.40 | 4.02 | 7   | 2.00  |
| 8  | 30 | 500  | 15 | 48.3 | 5.13 | 4.34 | 10  | 3.90  |
| 10 | 30 | 700  | 18 | 46.6 | 4.98 | 3.93 | 24  | 6.75  |
| 12 | 30 | 900  | 21 | 45.5 | 4.85 | 3.63 | 40  | 11.25 |
| 14 | 30 | 1050 | 24 | 44.8 | 4.78 | 3.45 | 67  | 16.75 |
| 16 | 30 | 1200 | 27 | 46.2 | 4.74 | 3.05 | 100 | 23.45 |

What is claimed is:

1. A process for preparing a biomass on a culture medium, the biomass being directly usable as a panification ferment without separating the biomass from the culture medium and without the addition of industrial yeast, said process comprising:

obtaining the culture medium;

inoculating the culture medium with at least one strain of yeast;

providing an air supply;

cultivating the strain of yeast on the culture medium in the presence of the air supply; and recovering the medium containing the biomass, wherein the culture medium comprises a medium free of any chemical additives obtained by;

preparing a dilute aqueous mixture comprising at least whole-flour or wheat germ, the mixture comprising starch and gluten;

adding at least one alpha-amylase and at least one amyloglucosidase to hydrolyze all of the starch in the mixture into fermentable sugar; and adding at least one proteolytic enzyme of food quality to gently hydrolyze at least part of the gluten in the mixture, thereby obtaining the culture medium.

2. The process of claim 1, wherein oxygen from the air supply is dissolved in the culture providing an oxygen partial pressure in the culture, the partial pressure of the oxygen dissolved in the culture being controlled by regulating the air supply in accordance with a previously defined slope, maintaining the culture in an aerobic metabolism limited in oxygen and maintaining the alcohol production in the range of 0.5 to 10 grams per liter.

3. The process of claim 1, wherein oxygen from the air supply is dissolved in the culture providing an oxygen partial pressure in the culture, the partial pressure of the oxygen dissolved in the culture being controlled by regulating the speed of agitation in accordance with a previously defined slope, maintaining the culture in an aerobic metabolism limited in oxygen.

4. The process of claim 1, wherein the culture is of the discontinued alimented type.

5. The process of claim 1, wherein the culture is grown without pH regulation.

6. The process of claim 1, wherein said yeast is a strain of *Saccharomyces cerevisiae*.

7. The process of claim 6, wherein said yeast is a strain of *Saccharomyces cerevisiae* isolated from a natural sponge.

8. Process of claim 7, wherein said yeast is the strain *Saccharomyces cerevisiae* steineri DSM 9211.

9. The process of claim 1, comprising the following steps:

introducing a first culture medium into a bioreactor;

inoculating said first culture medium with the yeast culture previously grown on second culture medium; and continuously alimenting the bioreactor with the second culture medium;

while maintaining:

a temperature of 30°±1° C.;

an aeration controlled by the partial pressure of oxygen; and an ethanol concentration between 0.5 and 10 grams/liter of culture.

10. The process of claim 1, wherein obtained product is concentrated by centrifugation or by filtration.

* * * * *